United States Patent [19]

Kysela et al.

[11] 4,216,173

[45] Aug. 5, 1980

[54] 1,1-DICHLORO-4-METHYL-3-HYDROXY-PENT-1-ENE

[75] Inventors: Ernst Kysela, Bensberg; Reinhard Lantzsch, Cologne; Erich Klauke, Odenthal, all of Fed. Rep. of Germany

[73] Assignee: Bayer Aktiengesellschaft, Leverkusen, Fed. Rep. of Germany

[21] Appl. No.: 7,271

[22] Filed: Jan. 29, 1979

Related U.S. Application Data

[62] Division of Ser. No. 707,781, Jul. 22, 1976, abandoned.

[30] Foreign Application Priority Data

Aug. 16, 1975 [DE] Fed. Rep. of Germany ....... 2536503

[51] Int. Cl.$^2$ .................... C07C 11/20; C07C 21/04

[52] U.S. Cl. .................... 260/654 R; 260/654 D; 260/655

[58] Field of Search ................ 260/654 R, 655, 654 D

[56] References Cited

U.S. PATENT DOCUMENTS

| | | | |
|---|---|---|---|
| 4,053,380 | 10/1977 | Fujita et al. | 260/654 R |
| 4,056,574 | 11/1977 | Holland et al. | 260/654 R |
| 4,078,008 | 3/1978 | Lantzoch et al. | 260/654 R |
| 4,081,488 | 3/1978 | Scharpf | 260/654 R |

*Primary Examiner*—Winston A. Douglas
*Assistant Examiner*—J. V. Howard
*Attorney, Agent, or Firm*—Sprung, Felfe, Horn, Lynch & Kramer

[57] ABSTRACT

A 1,1-dichloro-4-methyl-3-hydroxy-pent-1-ene and a process for its production.

6 Claims, No Drawings

1,1-DICHLORO-4-METHYL-3-HYDROXY-PENT-1-ENE

This is a division of application Ser. No. 707,781, filed July 22, 1976, now abandoned.

The invention relates to the new compound 1,1-dichloro-4-methyl-3-hydroxy-pent-1-ene, a process for its preparation and its use for the preparation of 1,1-dichloro-4-methyl-penta-1,3-diene.

According to the invention, 1,1-dichloro-4-methyl-3-hydroxy-pent-1-ene is prepared by hydrogenating 1,1-dichloro-4-methyl-pent-1-en-3-one with alkali metal borohydrides.

1,1-Dichloro-4-methyl-pent-1-en-3-one is known from J. Org. Chem. 32, 2661 (1967); it is obtainable in a simple manner from isobutyric acid chloride and vinylidene chloride. The course of the reduction, according to the invention, of 1,1-dichloro-4-methyl-pent-1-en-3-one is extremely surprising since ketones of this type are equally as reactive as acid chlorides [Izv. Adad. USSR 1962, 1248; J. Org. Chem. 32, 2661 (1967) and Zh. Org. Khim. 10 (1974) 11, 2293] and—since it is known that, in acid chlorides, sodium borohydride not only reduces the carbonyl group but also reacts with the chlorine atom [see J. Am. Chem. Soc. 78, 5079 (1956) and J. Org. Chem. 24, 109 (1959)]—it was therefore to be expected that it would not be possible to reduce the keto group to the alcohol group without at least side reactions taking place. Moreover, it was to be expected that the double bond would also be reduced during the reduction since it is known that in many cases double bonds which are conjugated with carbonyl groups are attacked by sodium borohydride. [See Chem. & Ind. 1954, 1482; J. Chem. Soc. 1957, 929; J. Am. Chem. Soc. 79, 3528 (1957) andJ. Am. Chem. Soc. 80, 1972 (1958)].

SUMMARY OF THE INVENTION

Broadly, this invention contemplates 1,1-dichloro4-methyl-3-hydroxy-pent-1-ene. This invention particularly contemplates a process for the preparation of 1,1-dichloro4-methyl-3-hydroxy-pent-1-ene which comprises contacting 1,1-dichloro-4-methyl-pent-1-en-3-one with an alkali metal borohydride under reducing conditions and recovering therefrom 1,1-dichloro-4-methyl-3-hydroxy-pent-1-ene. The latter compound is useful in the preparation of 1,1-dichloro-4-methylpenta-1,3-diene.

Surprisingly, however, it has been found that 1,1-dichloro-4-methyl-pent-1-en-3-one can be reduced with alkali metal borohydrides, preferably sodium borohydride, to give 1,1-dichloro-4-methyl-3-hydroxy-pent-1-ene in virtually quantitative yield.

An appropriate procedure is that the ketone is initially introduced in a water-miscible organic solvent, for example ethers, such as dioxane, tetrahydrofurane and dimethoxyethane; alcohols, such as methanol and ethanol, glycol, glycol monomethyl ether, glycol monoacetate or dimethylformamide, and the aqueous solution of the alkali metal borohydride is added dropwise. However, the dropwise addition of the alkali metal borohydride as a solution in an organic solvent in which it is soluble, for example, methanol, ethanol, dimethylformamide or dimethoxyethane, is also possible.

The reaction already proceeds at room temperature but, in order to accelerate the rate of reaction, it can be advantageous to carry out the reduction at elevated temperature, for example at 40°–100° C.

At least 0.25 ml of the borohydride are used per mol of ketone to be reduced. In order to achieve complete conversion, it is appropriate to employ a slight excess, preferably 0.3 to 0.5 mol of borohydride per mol of ketone. A larger excess is also not harmful.

The reaction mixture is worked up in a manner which is in itself known. 1,1-Dichloro-4-methyl-3-hydroxy-pent-1-ene can be purified by distillation.

1,1-Dichloro-4-methyl-3-hydroxy-pent-1-ene is a valuable intermediate product for the preparation of 1,1-dichloro-4-methyl-penta-1,3-diene. 1,1-Dichloro-4-methyl-penta-1,3-diene, which hitherto was obtainable only by an involved multi-stage reaction, which gave unsatisfactory yields and could not be employed for application on an industrial scale, can be prepared in good yields with the aid of 1,1-dichloro-4-methyl-3-hydroxy-pent-1-ene in a manner which can be carried out on an industrial scale.

The 1,1-dichloro-4-methyl-penta-(1,3)-diene can be reacted with diazoacetic-acid-ethylester to 2,2-dimethyl-3-(2',2'-dichlorovinyl)-cyclopropane-1-carboxylic acid-ethylester which can be hydrolyzed in known manner to the free acid [Coll. Czech. Chem. Comm. 24, 2230 (1959)].

These products are insecticides or intermediates for insecticides (DOS 23 26 077, DOS 24 18 950, DOS 24 36 178 or DOS 24 39 177). 1,1-Dichloro-4-methyl-3-hydroxy-pent-1-ene is converted into 1,1-dichloro-4-methyl-penta-1,3-diene by dehydration. The elimination of water is preferably carried out in the presence of customary dehydrating agents, for example acid salts, such as potassium bisulphate or sodium bisulphate; magnesium sulphate; salts of amines; iodine; phosphoric acid; carboxylic acids, such as oxalic acid, formic acid or acetic acid; carboxylic acid anhydrides, such as phthalic anhydride or succinic anhydride; metal oxides, such as aluminum oxide, zirconium-IV oxide and thorium-IV oxide; aluminum silicates or acid ion exchangers.

Depending on the agent used, the dehydrating agents are employed in amounts of 20–200, preferably 50–100, % by weight, relative to 1,1-dichloro-4-methyl-3-pent-1-ene.

The elimination of water is generally carried out at temperatures of 50°–350°, preferably of between 100° and 250° C.

The elimination of water can be carried out under reduced pressure but is preferably carried out under normal pressure. Where appropriate, it is also possible first to carry out the dehydration under normal pressure and then to distil off the diene and the water formed under reduced pressure. After separating off the water, the diene is isolated from the distillate by distillation.

EXAMPLE 1

9.5 g (0.25 mol) of sodium borohydride in 100 ml of water are added dropwise to a solution of 83.5 g (0.5 mol) of 1,1-dichloro-4-methyl-pent-1-en-3-one in 500 ml of dimethoxyethane. During the addition, the reaction mixture warms to 45° C. The course of the reduction is followed by IR spectroscopy (disappearance of the carbonyl band). When the reduction has ended, the reaction mixture is acidified with dilute sulphuric acid and extracted with ether. The ether solution is dried with sodium sulphate and freed from ether in a rotary evaporator. The residue is distilled under a water-pump vacuum.

80 g (95% of theory) of 1,1-dichloro-3-hydroxy-4-methyl-pent-1-ene are obtained in the form of colourless liquid (boiling point$_{10}$: 80°–85° C.).

The product displays as OH band in the IR spectrum; a carbonyl band is no longer present. The structure was confirmed by the nuclear magnetic resonance spectrum; the olefinic proton gives a doublet at $\delta$5.85 and 6.05 ppm (in CDCl$_3$).

EXAMPLE 2

84.5 g (0.5 mol) of 1,1-dichloro-3-hydroxy-4-methyl-pent-1-ene are added dropwise, at 200° C., whilst stirring, to 68 g (0.5 mol) of potassium bisulphate in a distillation apparatus. The reaction starts immediately. The water formed and the reaction product distil off together. 79 g of distillate are obtained. The water is separated off from the distillate and the organic phase is dried an distilled under a waterpump vacuum.

60 g (79.5% of theory) of 1,1-dichloro-4-methyl-penta-1,3-diene are obtained in the form of colorless liquid (boiling point$_{11}$: 57° C.).

EXAMPLE 3

84.5 g (0.5 mol) of 1,1-dichloro-3-hydroxy-4-methyl-pent-1-ene are mixed with 40 g of 85% strength phosphoric acid and the mixture is heated to 150°–180° C., whilst stirring. Water and the diene formed are distilled off continuously. When the reaction has ended, the water is separated off from the distillate and the organic phase is dried and distilled.

57 g (75.5% of theory) of 1,1-dichloro-4-methyl-penta-1,3-diene (boiling point$_{10}$: 55°–56° C.) are obtained.

EXAMPLE 4

7.6 g (0.2 mol) of sodium borohydride in 100 ml of methanol are added dropwise to a solution of 83.5 g (0.5 mol) of 1,1-dichloro-4-methyl-pent-1-en-3-one in 300 ml of methanol. The solution is kept at room temperature by cooling. The course of the reduction is followed by IR spectroscopy (disappearance of the carbonyl band). When the reaction has ended, the reaction mixture is acidified with dilute sulphuric acid and extracted with methylene chloride. The methylene chloride solution is freed from the solvent by distillation and the residue is subjected to fractional distillation under a waterpump vacuum.

78 g (92% of theory) of 1,1-dichloro-3-hydroxy-4-methyl-pent-1-ene are obtained in the form of a colorless liquid (boiling point$_{12}$: 84°–87° C.).

Analysis: C$_6$H$_{10}$Cl$_2$O (molecular weight 169.05) Calculated: C 42.6, H 5.95, Cl 41.95; Found: C 42.6, H 6.0, Cl 41.5.

What is claimed is:

1. A process for preparing 1,1-dichloro-4-methyl-penta-1,3-diene which comprises contacting 1,1-dichloro-4-methyl-3-hydroxy-pent-1-ene with a dehydrating agent under dehydration conditions.

2. A process according to claim 1 wherein said dehydrating agent is selected from the group consisting of an acid salt, a salt of an amine, iodine, a phosphoric acid, a carboxylic acid, a carboxylic acid anhydride, a metal oxide, an acid ion exchanger and aluminum silicate.

3. A process according to claim 2 wherein said dehydration agent is selected from the group consisting of potassium bisulfate, sodium bisulfate, magnesium sulfate, iodine, oxalic acid, formic acid, acetic acid, phthalic anhydride, succinic anhydride, aluminum oxide, zirconium-IV oxide and thorium-IV oxide.

4. A process according to claim 2 wherein the dehydration conditions include a temperature between 50° and 300° C.

5. A process according to claim 4 wherein the dehydration agent is present in an amount of 20–200% by weight relative to the 1,1-dichloro-4-methyl-3-hydroxy-pent-1-ene.

6. A process according to claim 1, wherein the 1,1-dichloro-4-methyl-3-hydroxy-pent-1-ene is produced by contacting 1,1-dichloro-4-methyl-pent-1-en-3one with an alkali metal borohydride under reducing conditions.

* * * * *